(12) United States Patent
Ham

(10) Patent No.: US 6,465,758 B1
(45) Date of Patent: Oct. 15, 2002

(54) LASER ASSISTED WIRE END FORMING PROCESS

(75) Inventor: Kevin L. Ham, Santa Clara, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/441,583

(22) Filed: Nov. 17, 1999

(51) Int. Cl.[7] .............................................. B23K 26/00
(52) U.S. Cl. .............................. 219/121.66; 219/121.65
(58) Field of Search ...................... 72/135; 219/121.65, 219/121.66, 121.6, 121.85

(56) References Cited

U.S. PATENT DOCUMENTS

| | | | | |
|---|---|---|---|---|
| 3,711,908 A | * | 1/1973 | Broers | .................... 219/121.85 |
| 3,718,968 A | * | 3/1973 | Sims et al. | |
| 3,826,000 A | * | 7/1974 | Du Rocher et al. | |
| 4,256,948 A | * | 3/1981 | Wolf et al. | ............. 219/121.65 |
| 5,105,062 A | * | 4/1992 | Jones et al. | ............. 219/121.85 |
| 5,690,842 A | * | 11/1997 | Panchison | |
| 6,133,540 A | * | 10/2000 | Weiss et al. | |

FOREIGN PATENT DOCUMENTS

| | | | | |
|---|---|---|---|---|
| JP | | 4-94143 | * 3/1992 | ............. 219/121.66 |

* cited by examiner

Primary Examiner—Geoffrey S. Evans
(74) Attorney, Agent, or Firm—Fulwider Patton Lee & Utecht, LLP

(57) ABSTRACT

A process for forming an end of a wire to be used in a medical procedure comprising the steps of cutting the wire and heating the cut end with laser energy to form a smoothed end or a smoothed ball end. By using a minimal amount of energy, a smoothed end is formed. By using a greater amount of energy, a smoothed ball end is formed to provide additional mass for a subsequent welding operation. A fixture is used to position the wire to facilitate this process.

12 Claims, 2 Drawing Sheets

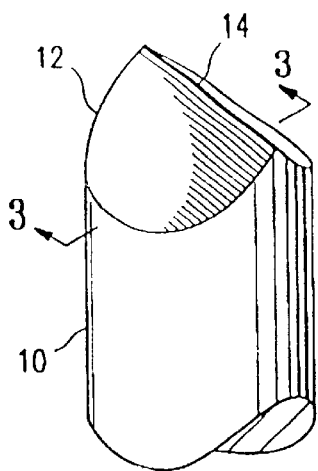
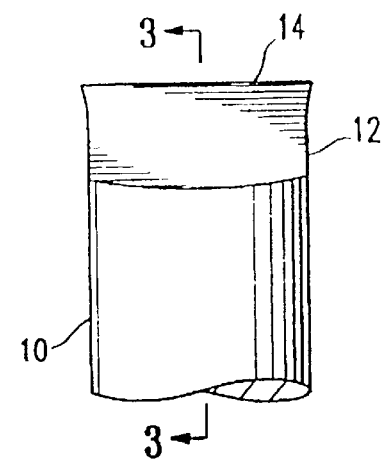
FIG. 1
PRIOR ART
FIG. 2
PRIOR ART
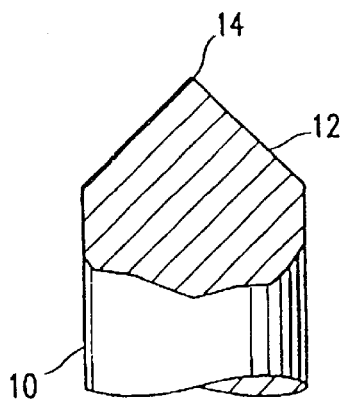
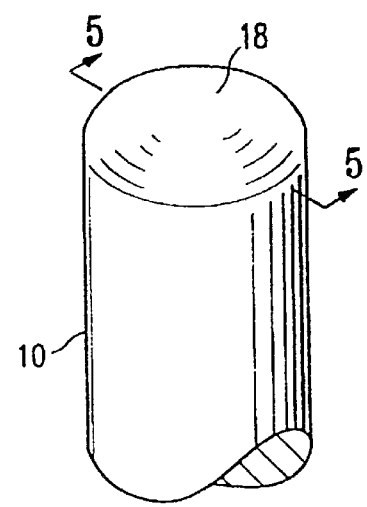
FIG. 3
PRIOR ART
FIG. 4
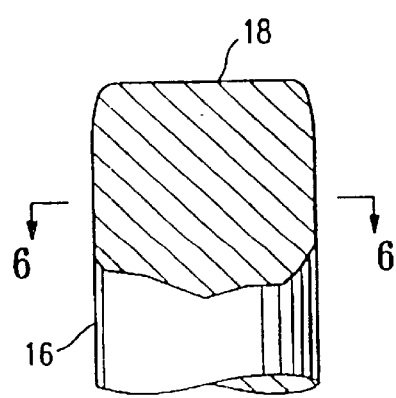
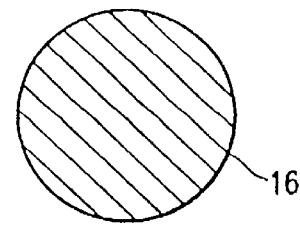
FIG. 5
FIG. 6

LASER ASSISTED WIRE END FORMING PROCESS

BACKGROUND

Metallic wires are widely used in medical procedures, a common example being the guidewires used to locate intravascular devices such as angioplasty catheters. Conventional processes for forming such wires often include the step of cutting the components of the guidewire with diagonal pliers or the like. However, the cut end often exhibits sharp artifacts or burrs. This sharp edge can damage other materials or components used in conjunction with the wire. For example, the relatively soft polymeric materials of an angioplasty catheter could be easily damaged by such a burr or sharp edge. Likewise, the sharp edge also poses risk to personnel handling the wire or to the patient undergoing the medical procedure. Conventional means of removing these sharp edges include sanding the cut end. This process often produces undesirable microscopic grooves in the wire, leaves abrasive debris and raises manufacturing costs since it is time consuming and labor intensive and uses consumables.

Additionally, wires used in medical devices are often welded to attach another component to the wire end. For example, to add stiffness to the distal portion of a catheter, a hypotube can be welded to the end of a wire and positioned in the distal end of the catheter. However, the welding process often has the effect of removing material from the wire adjacent the welding area. Removal of material, or undercutting, in the weld area leads to decreased strength or altered bending properties and can lead to failure of the wire.

Accordingly, there is a need for improved wire forming processes that produce a non-traumatic cut end. There is also a need for wire forming processes that facilitate the welding of an additional component to the cut end of the wire. There is a similar need for wires that embody these features and a fixture for carrying out the processes.

SUMMARY

The invention is directed to a process for forming a wire for use in a medical or intracorporeal device including cutting the wire to form a cut end and smoothing the cut end by heating the cut end to form a body of molten material which is cooled to solidify into a smoothed end. Heating the cut end can be achieved by applying laser energy. Any suitable type of laser energy may be used, delivered in pulses or in a continuous wave (CW) mode.

The invention is also directed to a process for forming a wire for use in an intracorporeal or medical device which is to be welded to an additional component. The process can include cutting the wire to form a cut end and forming a smoothed ball end at the cut end by heating the cut end to form a ball of molten material which is cooled so as to solidify. Again, heating the cut end of the wire can be achieved by applying laser energy. The process may also include abrading the cut end to reduce energy reflection prior to heating the cut end, particularly when laser energy is used.

The invention is also directed to a wire for use in a medical procedure or as a component in a medical device, the wire having a smoothed end formed by the process discussed above. Additionally, the invention is directed to a wire to be welded to an additional component with the wire having a smoothed ball end formed by the appropriate process described above. In one embodiment, a process having features of the invention can be carried out with a fixture for heating the end of a wire. The fixture can have a wire guide for accepting and clamping the wire in a desired position having a discharge axis, a source of heating energy having a focal point coaxially aligned with the discharge axis of the wire guide, and a removable stop that locates the end of the wire at the focal point of the source of heating energy.

BRIEF DESCRIPTION OF THE DRAWINGS

FIG. 1 is a perspective view of a wire end formed by mechanical cutting.

FIG. 2 is an elevational view in partial section of the wire end of FIG. 1.

FIG. 3 is a transverse cross sectional view of the wire end of FIG. 2 taken along lines 3—3 of FIG. 2.

FIG. 4 is a perspective view of a wire having a radiant energy smoothed end.

FIG. 5 is an elevational view in partial section of the wire end of FIG. 4.

FIG. 6 is a transverse cross sectional view of the wire end of FIG. 5 taken along lines 6—6 of FIG. 5.

DETAILED DESCRIPTION

Figure 7:
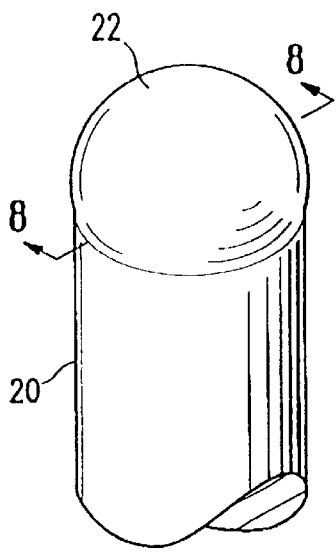
FIG. 7 is a perspective view of a wire having a smoothed ball end.

FIGS. 1–3 show the end of a wire 10 formed by conventional methods. A wire 10 as shown in FIG. 1 could be used as a component in a wide variety of medical devices such as balloon angioplasty catheters, stent delivery catheters, guidewire exchange catheters, guidewires or the like. Wire 10 can have a broad range of materials and dimensions. For use as a core member of a coronary angioplasty guidewire, wire 10 could be made from a variety of stainless steels including 304, 304V, 316L, high tensile, precipitation hardenable and the like. Such a wire 10 could have transverse cross section that is circular, as shown, but could also be elliptical, square, rectangular or any other suitable configuration. The transverse dimension of such a wire 10 can be from about 0.001 to about 0.05 inch, specifically about 0.002 to about 0.02 inch, and more specifically about 0.010 to about 0.016 inch. The wire 10 has a cut end 12 that exhibits razor sharp artifacts or edges and burrs 14 formed by the shearing action of diagonal pliers that can be used to cut the wire.

FIGS. 4–6 show wire 10 having a smoothed end 18 formed by applying energy to the cut end 12. Wire end 18 can be formed with a relatively low dose of energy that forms an end with edges having a smooth radius. The smoothed end 18 is formed when a source of heating energy is directed onto cut end 12 to form a body of molten material which is then cooled or allowed to cool so as to solidify. The heating energy used in the process of the invention can be from a laser source. Suitable lasers include Neodymium: Yitrium-Aluminum-Garnet or Carbon Dioxide, however any other form of energy capable of melting the cut end 12 of the wire 10 and forming a smoothed end 18 or smoothed ball end 22 can be used. One or more pulses may be used to deliver a suitable dosage, which will depend on the size of wire 10 or 20 and an amount of smoothing desired. For a CW laser, the exposure time can be adjusted along with the power level to achieve the desired result. These parameters may be computed from the type of metal from which the wire, its diameter and the source of energy or may easily be determined empirically.

A JK702 Neodymium YAG pulsed laser with an output of approximately 100 watts manufactured by Lumonics® Corporation can be used as a heating energy source to practice an embodiment of the invention. The beam from such a laser can be focused through a lens having a focal length of about 90 to about 110 mm and the focused beam directed substantially to the cut end 12 of wire 10. If wire 10 is made from stainless steel with a diameter of about 0.005 to about 0.007 inch, an energy dose of about 0.2 to about 0.3 Joules can be delivered to the cut end 12 to create a radiant energy smoothed end 18 such as that shown in FIG. 4. Additional laser parameters for delivery of such an energy dosage include a pulse length of about 2.5 to about 3.5 msec, a pulse frequency of about 4 to about 6 Hz and a pulse height of about 38.7 percent. In one embodiment, argon gas, or any suitable inert gas is passed over the cut end 12 during formation of the radiant energy smoothed end 18. The argon gas can be passed over the cut end 12 at a rate of about 10 to about 20 cubic feet per hour. The argon gas can be delivered by a length of flexible tubing with an output end disposed adjacent to the cut end 12.

Figure 8:
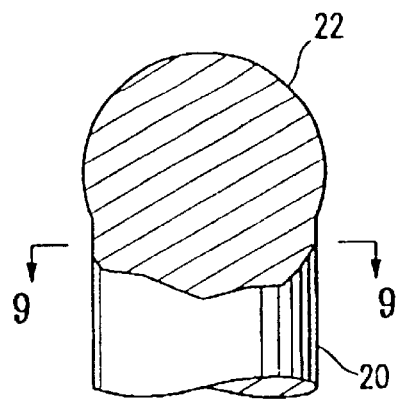
FIG. 8 is an elevational view in partial section of the wire end of FIG. 7.
Figure 9:
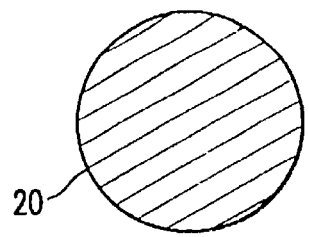
FIG. 9 is a transverse cross sectional view of the wire end of FIG. 8 taken along lines 9—9 of FIG. 8.

FIGS. 7–9 show a wire 20 having a smoothed ball end 22 formed by a relatively high dose of heating energy. Smoothed ball end 22 has additional mass to allow a subsequent welding procedure to attach an additional component such as a hypotube (not shown) to smoothed ball end 22 without undercutting guidewire 20. Varying the amount of energy applied to the smoothed ball end 22 of the guidewire develops the desired size ball at the cut end. If a JK702 ND:YAG pulsed laser, as described above, is used with a similar focusing lens and set up, a radiant energy dosage of about 0.25 to about 1.0, specifically about 0.35 to about 0.45 Joules can be delivered. Such a radiant energy dosage would be appropriate to form a smoothed ball end 22 on a wire 20 made from stainless steel and having a diameter of about 0.005 to about 0.007 inch.

Figure 10:
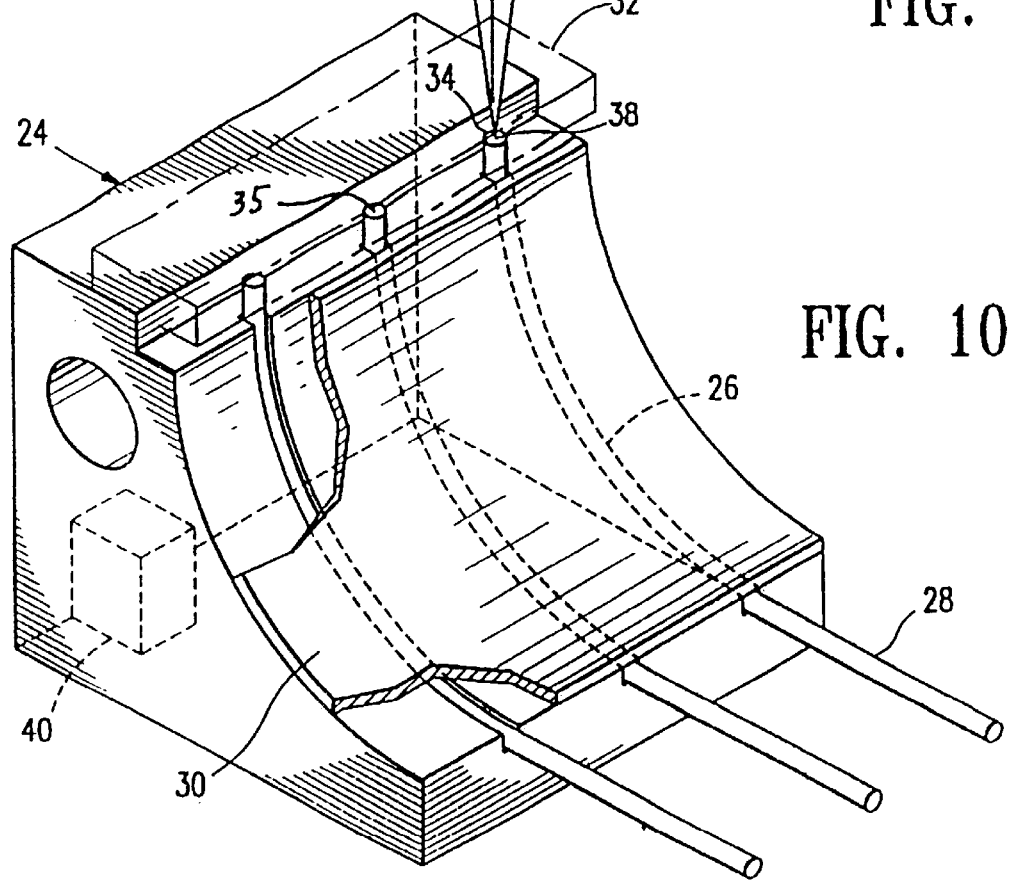
FIG. 10 is a perspective view of a fixture suitable for applying heating energy to an end of a wire.

FIG. 10 shows a fixture 24 for use in forming the wires having features of the invention. Fixture 24 generally comprises a wire guide 26 shown in FIG. 10 as a groove cut into fixture 24 that is slightly larger in transverse dimension than wire 28. Wire guide 26 is configured to slidingly accept wire 28 and clamp 30 is used to temporarily secure wire 28 in a desired position. Clamp 30 is shown in FIG. 10 as a curved body which conforms to the fixture 24 adjacent the wire guide 26. Pressure can be applied by clamp 30 to wire 28 forcing wire 28 into guide 26 and temporarily securing wire 28 within guide 26 by mechanical clamping action. Clamp 30 can, however, can be configured to operate by any suitable means which temporarily secures wire 28 to guide 26, including frictional force created by the spring force of straight wire 28 within the curved wire guide 26. Stop 32 (shown in phantom) allows wire 28 to be advanced through guide 26 until cut end 34 abuts stop 32. Stop 32 is preferably slidably or pivotally attached to fixture 24 so that it may be moved out of the way once wire 28 so as not to impede the delivery of energy to cut end 34. Alternatively, stop 32 simply may be removable. Other suitable means of positioning and temporarily securing wire 28 will be readily apparent to one of skill in the art.

In the embodiments shown in FIG. 10, guide 26 of fixture 24 is configured such that cut end 34 of wire 28 is oriented vertically. Vertical orientation of cut end 34 can be particularly important when creating a smoothed ball end 22, such as is shown in FIGS. 7–9. Vertical orientation of cut end 34 prevents the molten ball of metal from sagging laterally under the force of gravity when the smoothed ball end 22 is in a molten state during the process.

Heating energy source 36 is coaxially aligned with a vertically oriented discharge axis 27 of guide 26. Stop 32 is configured to position wire 28 so that cut end 34 is approximately located at a focal point 38 of heating energy source 36. In some embodiments, fixture 24 further comprises a registration notch 40 to repeatably position fixture 24 with respect to heating energy source 36. Although it is not shown in FIG. 10, fixture 24 can be secured to a translation beam which is configured to translate accurately back and forth in one dimension. The translational movement of the translation beam can optionally be carried out under the impetus of a servo motor. The servo motor can be controlled by a CNC controller that is indexed to stop at predetermined intervals that correspond to the centerlines of the various cut ends 34 and 35 shown in FIG. 10. In this way, a first cut end 34 can be aligned substantially in the path of the focal point 38 of heating energy 36, such as might be produced by the laser system described above, and a dosage of heating energy subsequently delivered to the first cut end 34.

The dosage of heating energy 36 can be configured to form either a smoothed end 18 or a smoothed ball end 22 as described above. The servo motor can then be activated by the CNC controller to translate the translation beam and fixture 24 laterally and stop when a second cut end 35 is substantially aligned in the focal point 38 of radiant energy 36 while the heating energy 36 is inactive. The heating energy 36 can then be activated and another dosage of heating energy 36 can then be administered to the second cut end 35 to achieve a desired result.

The dosages of heating energy and translation of the fixture 24 can be controlled by the CNC controller in a manual mode, or in an automated mode whereby after a dosage of heating energy is applied to a cut end, the fixture 24 is automatically translated to align the next cut end and a second dosage of heating energy applied automatically upon alignment. This process can be carried out for any desired number of iterations so as to automate the process. Also, fixture 24 could be configured in an annular carousel that continuously rotates, loads wires 10 having cut ends 12 into the fixture, applies a dosage of heating energy to achieve a desired result, then ejects the finished wires.

A process having features of the invention generally includes cutting the wire 10 to form a cut end 12. The cut end 12 is then subjected to heating energy to form a smoothed end 18 or smoothed ball end 22. Applying a relatively small amount heating energy forms a correspondingly small smoothed ball end 22. Applying a larger amount of heating energy forms a larger smoothed ball end 22 to provide additional mass for a subsequent welding operation. Fixture 24 may be used in these processes by advancing wire 28 through guide 26 until end 34 hits stop 32. Clamp 30 holds wire 28 in this desired position and stop 32 is moved to allow application of heating energy to end 34. Heating energy source 36 is then operated to produce the desired size smoothed ball end 18. Single or multiple pulses of heating energy rapidly heat and thus melt the wire at cut end 34. As this pool of molten metal cools, surface tension will pull the material into a uniform ball.

While less important when simply smoothing the cut end, forming a specific size ball end is more important for wires intended to be subsequently welded. To reduce variability in energy dose, cut end 34 can be abraded to minimize reflection of the applied energy. When creating a smoothed end 18, the orientation and shape of the cut end 12 is relatively unimportant. However, when forming a smoothed ball end 22 for a subsequent welding operation, the cut end 12 of the wire can be made relatively smooth and perpendicular prior to heating. This can be achieved by exposing the cut end 12 to a flat grinding surface prior to exposing the cut end 12 to heating energy. This can help keep the dimensions of the resulting smoothed ball end 22 uniform and symmetric.

Described herein are preferred embodiments, however, one skilled in the art that pertains to the present invention will understand that there are equivalent alternative embodiments.

What is claimed is:

1. The process of forming a wire having a longitudinal axis for use in a medical device comprising:
   a) cutting the wire to form a cut end;
   b) fixing the wire with the cut end in a vertical orientation;
   c) directing a laser beam which is aligned with the longitudinal axis of the wire toward the cut end of the wire and thereby forming a body of molten material; and
   d) cooling the molten material into a smoothed end.

2. The process for forming a wire having a longitudinal axis to be welded to an additional component of a medical device comprising:
   a) cutting the wire to form a cut end;
   b) fixing the wire with the cut end in a vertical orientation;
   c) directing a laser beam which is aligned with the longitudinal axis of the wire toward the cut end of the wire and thereby forming a body of molten material; and
   d) cooling the molten material into a smooth end.

3. The process of claim 2 further comprising abrading the cut end prior to forming the smoothed end.

4. A fixture for heating and melting the end of a wire for use in a medical device, comprising:
   a) a wire guide for positioning the wire in a desired position having a vertical discharge axis;
   b) a source of heating energy having a focal point of coaxially aligned with the discharge axis of the wire guide; and
   c) a stop that locates the end of the wire at the focal point of the source of heating energy.

5. The fixture of claim 4 wherein the source of heating energy comprises a laser.

6. The fixture of claim 5 wherein the laser is a ND:YAG laser.

7. The fixture of claim 4 wherein the discharge axis is substantially vertical.

8. The fixture of claim 4 further comprising a clamp for temporarily securing the wire within the wire guide.

9. A method for forming an end of a wire for use in a medical device comprising:
   a) providing a fixture having a wire guide for positioning the wire in a desired position having a discharge axis, a source of heating energy having a focal point coaxially aligned with the discharge axis of the wire guide, and a stop that locates the end of the wire at the focal point of the source of heating energy;
   b) positioning the wire in the wire guide with the end of the wire abutting the stop;
   c) moving the stop to expose the end of the wire;
   d) activating the source of heating energy to form a body of molten material on the end of the wire; and
   e) cooling the end of the wire.

10. The method of claim 9 wherein the discharge axis of the fixture is substantially vertical prior to step d).

11. The method of claim 9 further comprising abrading the end of the wire prior step d).

12. The method of claim 9 wherein the fixture further comprises a clamp for temporarily securing the wire to the wire guide and the wire is temporarily secured to the wire guide after being positioned in the wire guide.

* * * * *

UNITED STATES PATENT AND TRADEMARK OFFICE
CERTIFICATE OF CORRECTION

PATENT NO. : 6,465,758 B1
DATED : October 15, 2002
INVENTOR(S) : Kevin L. Ham

It is certified that error appears in the above-identified patent and that said Letters Patent is hereby corrected as shown below:

<u>Title page,</u>
Item [57], ABSTRACT,
Line 2, change "comprising", to read -- includes --.

Signed and Sealed this

Fourth Day of March, 2003

JAMES E. ROGAN
*Director of the United States Patent and Trademark Office*